United States Patent [19]

Hill et al.

[11] 4,301,412

[45] Nov. 17, 1981

[54] LIQUID CONDUCTIVITY MEASURING SYSTEM AND SAMPLE CARDS THEREFOR

[75] Inventors: Jeremy R. Hill, Weston; Allen E. Meyer, Greenwich, both of Conn.

[73] Assignee: United States Surgical Corporation, Norwalk, Conn.

[21] Appl. No.: 89,086

[22] Filed: Oct. 29, 1979

[51] Int. Cl.³ ............................................. G01R 27/22
[52] U.S. Cl. .................................... 324/442; 128/637; 73/343.5; 324/448
[58] Field of Search ............... 324/442, 441, 446, 447, 324/448, 450, 65 R, 64; 128/637, 669; 29/592 R, 876, 877; 73/344, 343.5

[56] References Cited

U.S. PATENT DOCUMENTS

| Re. 30,007 | 5/1979 | Steuer et al. | |
|---|---|---|---|
| 2,621,235 | 12/1952 | Jewell | 324/441 |
| 2,764,892 | 10/1956 | Rosenthal | 324/441 X |
| 3,471,393 | 10/1969 | Ingruber | 324/441 X |
| 3,781,659 | 12/1973 | Ur | |
| 4,123,701 | 10/1978 | Josefsen et al. | |

OTHER PUBLICATIONS

Changes in the Electrical Impedance of Blood during Coagulation, Nature, vol. 226, Apr. 18, 1970, pp. 289 & 270.

Primary Examiner—Stanley T. Krawczewicz
Attorney, Agent, or Firm—Fleit & Jacobson

[57] ABSTRACT

A system for measuring a parameter of a liquid sample, such as the hematocrit and an approximation of hemoglobin for a blood sample. The system basically comprises a hand-held instrument and a disposable sample card. The instrument accepts the disposable sample card, which is used for the one-time conveyance and application of a liquid sample, such as blood, to the instrument. The instrument has provision for digital displays for readouts. The disposable sample card is a micro-volume conductivity cell precision molded from plastic with built-in stainless steel electrodes. The instrument basically comprises an electronic portion for processing data obtained from the liquid sample on the sample card, a front-end mechanism for positioning the sample card within the instrument, and a digital display for displaying in eye-readable form the results of a parameter measurement made in the instrument.

9 Claims, 19 Drawing Figures

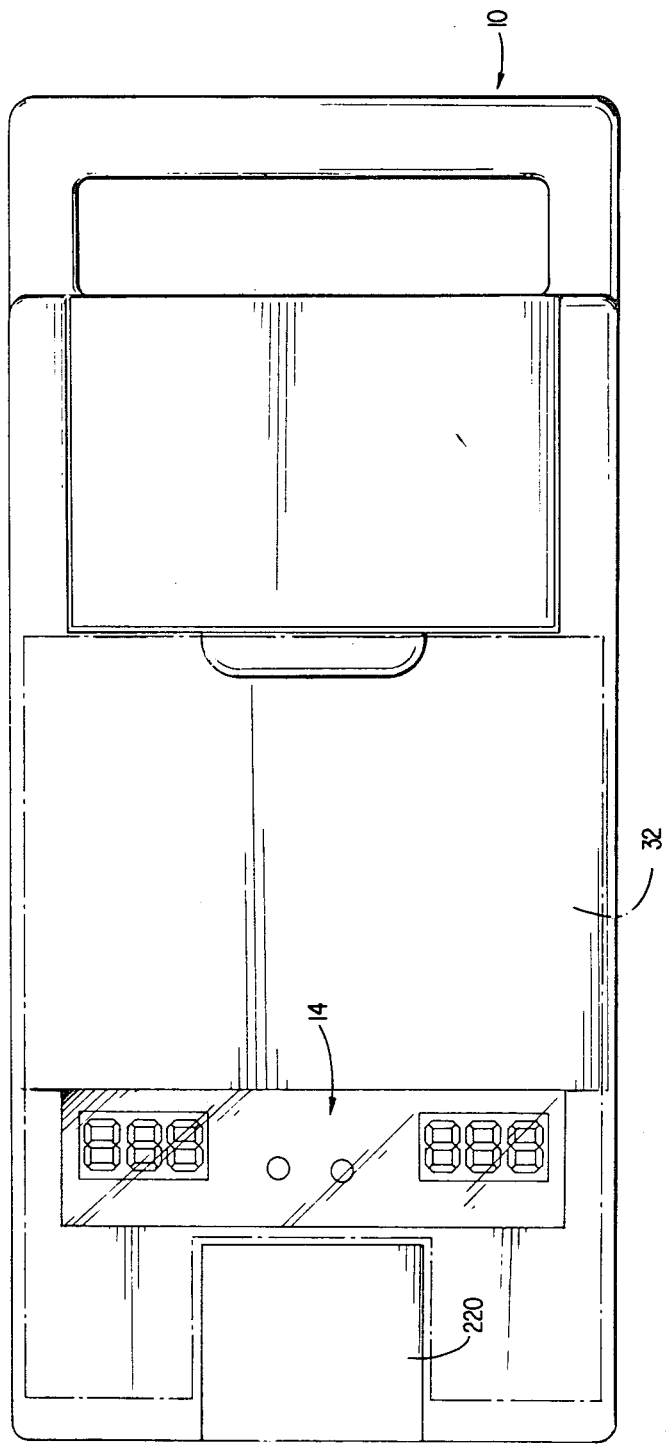
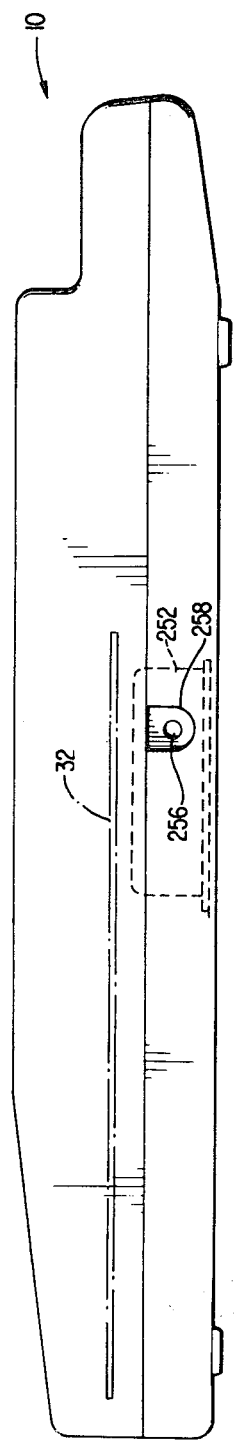
FIG. 2
FIG. 3

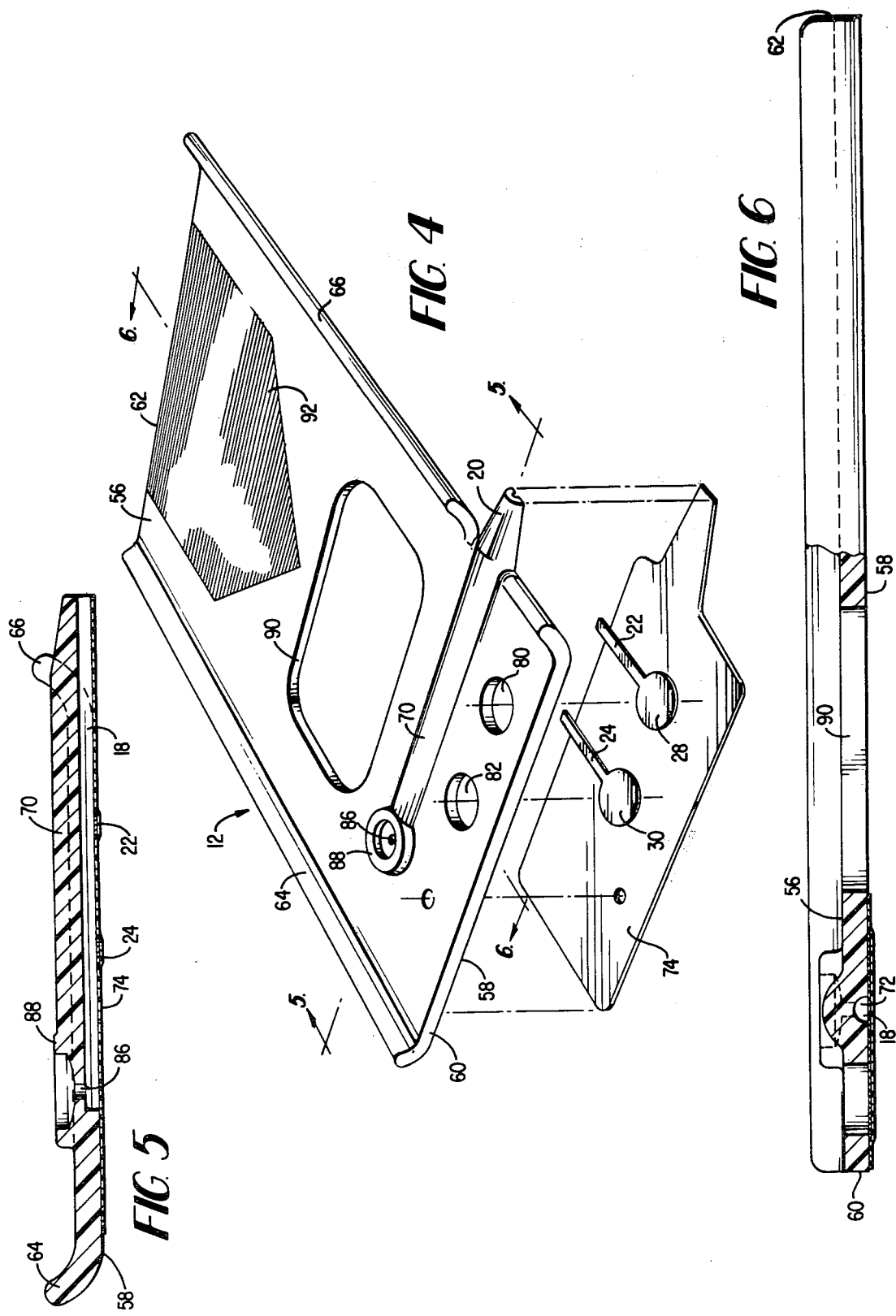

LIQUID CONDUCTIVITY MEASURING SYSTEM AND SAMPLE CARDS THEREFOR

BACKGROUND OF THE INVENTION

1. Field of the invention

This invention relates to systems for measuring conductivity of bodily fluids, in general, and to a system for automatically measuring hematocrit and giving an approximation of hemoglobin, in particular.

2. Background of the prior art

Various methods and apparatus are known for studying liquid samples. Some involve centrifugation, others utilize agitation, and there are still others which depend upon the elecrical characteristics of the sample being tested. In virtually all of these known techniques, especially those in the medical field, it is of prime importance to maintain isolation between samples. A still further problem relates to the protection of the technician against contracting infectious diseases from the samples under test. With the known methods and apparatus, very little protection is afforded.

An example of an apparatus for studying the electrical characteristics of blood can be found in U.S. Reissue Pat. No. Re. 30,007, issued to Steuer et al on May 22, 1979. This apparatus includes a rod-like probe having two conductive electrodes at the tip of the probe. A blood sample is associated with the electrodes of the probe, and an electrical current is applied across the blood for the purpose of hematocrit determinations. Obviously, the probe must be thoroughly cleaned between tests to ensure accurate test results.

An example of a disposable blood sample card is shown in U.S. Pat. No. 4,123,701, filed on July 1, 1976, to inventors Josefson and Veth, and assigned to United States Surgical Corporation. The blood sample card described therein is a disposable blood sample carrier comprising a substantially planar base portion made of an electrically insulating material. The card is sterilized, pre-packaged and disposable after a single use. In the base portion of the card is a well to receive the blood sample. The well is sized so as to accommodate approximately one drop of blood, and a well volume on the order of 0.05 ml is described. Electrodes are positioned in the well and are adapted to be connected to an instrument that evaluates the electrical characteristics of the blood sample by means of electrical circuitry, as disclosed, for example, in the aforementioned U.S. Reissue Pat. No. Re 30,007.

The measuring instrument and blood sample card just described, are considered to be exemplary of the present state of the art. Nevertheless, there is a need for a system which provides a simplified, safe and accurate electrical evaluation of liquid samples. The present invention is directed toward filling that need.

SUMMARY OF THE INVENTION

The present invention generally relates to testing of liquid samples by electrical means. Particularly, use is found for the invention in the medical field, especially in studying the electrical conductivity of whole blood samples and the like.

Specifically, the system, according to the subject invention, comprises an instrument and a disposable blood sample card or carrier. The instrument is a hand-held, battery-operated device used for the fast and simple measurement of blood conductivity, such as hematocrit. The instrument accepts the disposable sample card, which is used for the one time conveyance and application of a liquid sample, such as blood, to the instrument.

The instrument has provision for digital displays for read-outs of hematocrit and the approximate equivalent of hemoglobin. There are no external switches on the instrument, and power is automatically applied when the disposable sample card is inserted into the instrument.

The measurement technique employed by the system is based on the well-known conductivity principle. Briefly, this principle states that blood serum acts as a conductor, while the red blood cells act as insulators. If an alternating current is passed through a whole blood sample of well defined volume and temperature, its conductivity will be inversely related to the number of red blood cells per unit volume. Therefore, if the conductivity of the blood sample is known, the hematocrit can be determined.

Blood serum also exhibits a rather extreme temperature coefficient which directly affects blood conductivity. Therefore, the system of the present invention also measures the temperature of the blood sample and, using this data together with the conductivity measurement, calculates the hematocrit value. An approximation of hemoglobin is also provided. In the present system, hemoglobin is determined by dividing the hematocrit value by 3.

In a preferred embodiment, the blood sample card is a micro-volume conductivity cell precision molded from plastic with built-in stainless steel alloy electrodes. Basically, the sample card comprises a planar base portion on which is defined a capillary tube. A nozzle located at the end of the capillary tube provides an entrance for a blood sample to enter the capillary tube. First and second electrodes are disposed within the capillary tube in a spaced relationship and define a volume within the capillary tube. This volume, defined between the two electrodes within the capillary tube constitutes the conductivity cell.

Each of the electrodes is electrically connected to a conductive pad that provides a means for associating the blood sample with the electronics contained in the instrument to make a conductivity measurement of the sample.

The instrument, in accordance with the teachings of the subject invention, basically comprises an electronic portion for processing data obtained from the blood sample on the sample card, a front end mechanism for positioning the blood sample card within the instrument, and a digital display for displaying in eye-readable form the results of a hematocrit measurement made in the instrument.

The front end mechanism of the instrument contains an indexing member associated with a block or base portion so that proper insertion of the sample card within the instrument is assured. The base portion is preferably made of a material exhibiting excellent heat-conducting characteristics. One such material is aluminum.

A roller assembly within the instrument holds the sample card in intimate contact with the top surface of the base portion. Also provided as part of the front end mechanism is a generally L-shaped bracket which contains electrical contact assemblies. The L-shaped bracket is pivotally mounted in the mechanism so that, upon insertion of the sample card, the contact assemblies are brought into electrical association with the pads on the disposable sample card.

The distance between the blood sample in the capillary tube and the bottom of the disposable sample card is kept to a minimum through the use of a very thin sheet of plastic material, such as Mylar. This is done so that, when the sample card is positioned within the instrument, the blood sample is in close contact with the base portion of the front end mechanism. In this way, the blood sample, after a very short period of time, assumes the temperature of the base portion. A thermistor is imbeded in the base of the front end mechanism near where the blood sample will be located when the sample card is inserted into the instrument. In this way, data relating to the temperature of the base portion, which is also the temperature of the blood sample, can be presented to the electronic circuitry within the instrument for subsequent processing.

Each of the electrical contact assemblies contains a lead which is presented to the electronic circuitry to accomplish the application of an excitation current across the blood sample and the attendant measurement of the conductivity of the blood sample.

The construction of the disposable sample card produces many observable advantages over similar prior art devices. The disposable sample card readily capillarizes the blood sample and makes it easy for sample collection directly from a patient or from a test tube. The disposable sample card is translucent and the capillary section provides a magnifying area so that any air pockets or other discontinuities in the blood sample are readily apparent. On the top surface of the sample card, the magnifying area of the capillary section provides a bump, which acts as a locator once the disposable sample card is pushed into the front end mechanism of the instrument. The distance between the bottom of the disposable blood sample carrier and the blood sample in the capillary tube is kept to a minimum so that there is excellent heat transfer between the blood sample and the heat-conducting base portion of the front end mechanism. In addition, the sample card contains a cut-out near the blood sample which acts to decrease the thermal mass in the area of the blood sample, thus, promoting heat transfer between the blood sample and the base portion.

The instrument, associated with the sample card, is powered by a self-contained, rechargeable battery and is completely portable. There are no switches, adjustments or calibrations available to the operator, not even a power switch. Insertion of the disposable sample card turns the power on and removal of the sample card turns the power off.

It is thus a principle object of the present invention to provide a system for rapid and accurate measurement of conductivity of a liquid sample.

It is another object of the present invention to provide a completely portable system employing a disposable sample card for measuring hematocrit within a blood sample taken directly from a patient or from a test tube.

It is still an object of the present invention to provide a disposable sample card for receiving liquid samples and for determining a characteristic of such samples through electrical means.

It is yet an object of the present invention to provide a technique for testing body fluids in a manner which avoids cross-contamination of samples and which minimizes the possibility of its technician contracting a disease.

It is a further object of the present invention to provide a disposable sample card for electrical evaluation of body fluids, such as hematocrit determinations.

It is still another object of the present invention to provide a disposable sample card that is easy to manufacture at a minimum cost.

It is yet another object of the present invention to provide an instrument which contains a mechanism that responds to the insertion of a disposable sample card by activating the instrument to make an electrical measurement of the liquid sample contained on the card.

These and other objects of the present invention, as well as many of the attendant advantages thereof, will become more readily apparent when reference is made to the following description, taken in conjunction with the accompanying drawings.

BRIEF DESCRIPTION OF THE DRAWINGS

FIG. 2 is a top plan view of the instrument shown in FIG. 1 with the front end mechanism cover in place.

FIG. 3 is a side plan view of the instrument shown in FIG. 1.

FIG. 4 is an exploded perspective view showing the elements constituting a preferred embodiment of a disposable sample card.

FIG. 5 is a view taken along lines 5—5 of FIG. 4.

FIG. 6 is a view taken along lines 6—6 of FIG. 4.

DETAILED DESCRIPTION OF THE DRAWINGS

Figure 1:
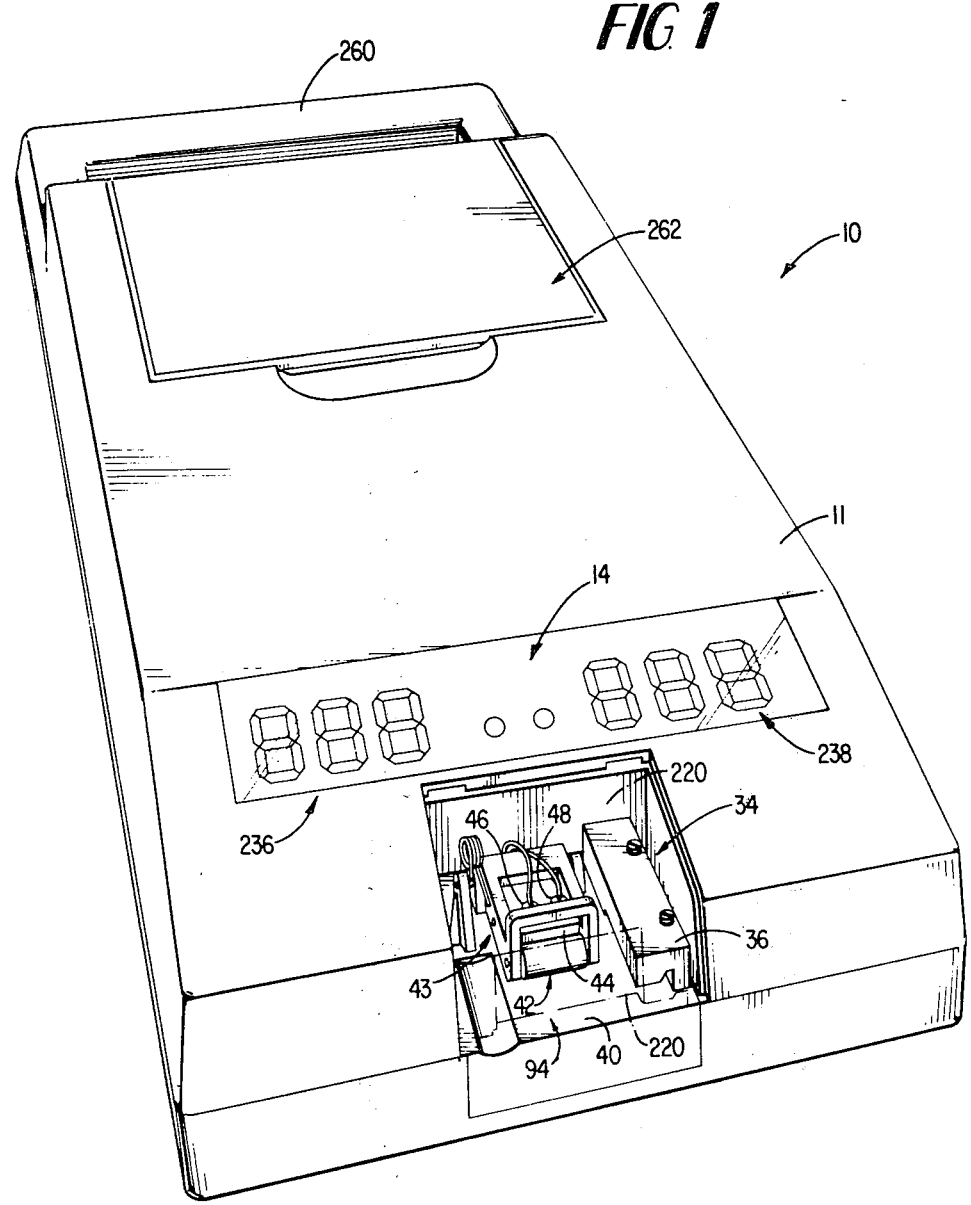
FIG. 1 is a perspective view showing a preferred embodiment for the instrument with the front end mechanism cover in phantom for use in the liquid conductivity measuring system.
Figure 7:
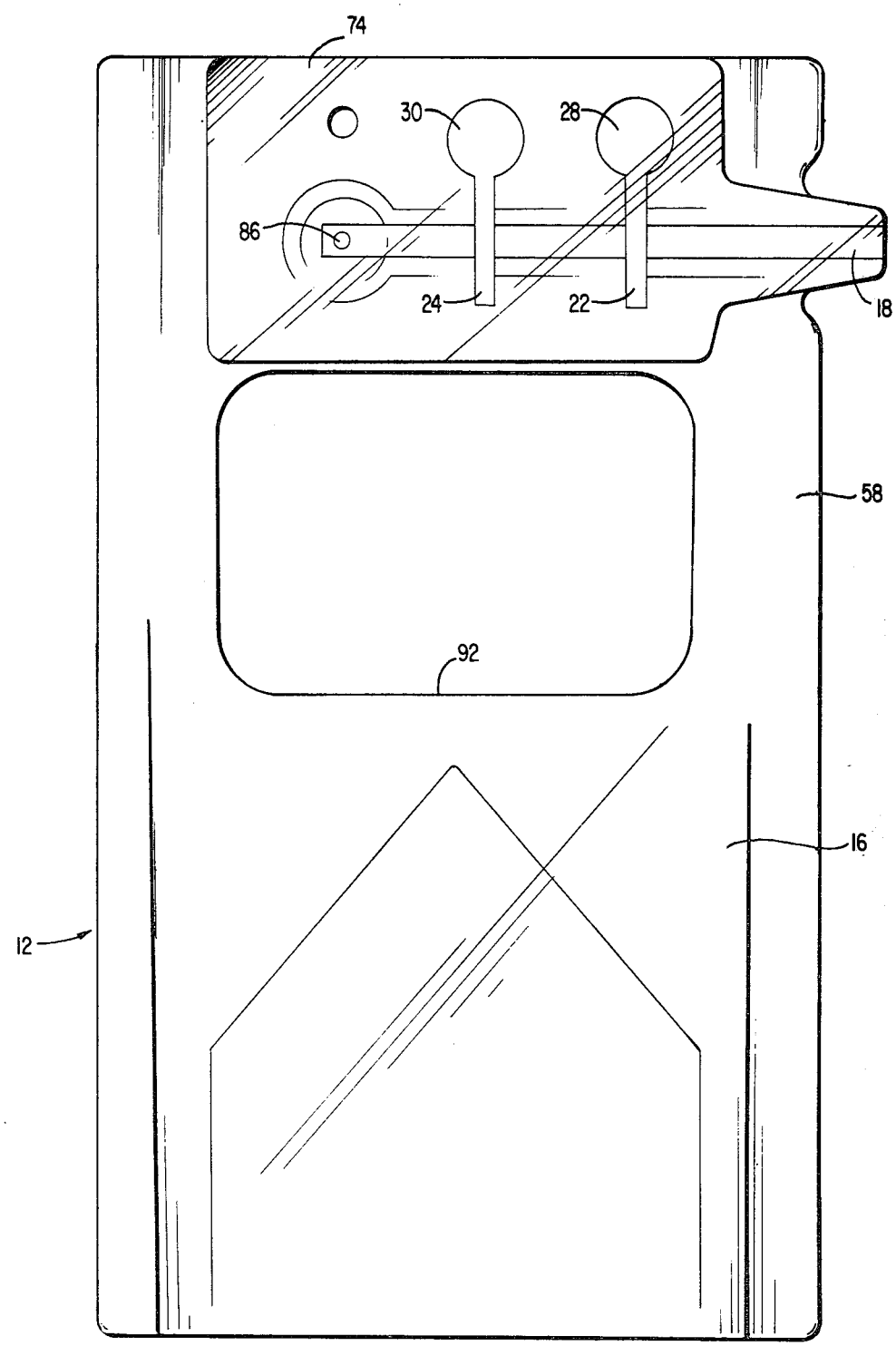
FIG. 7 is a bottom plan view of the disposable sample card illustrated in FIG. 4.

The present invention generally relates to testing of liquid samples by electrical means. Particularly, use is found for the invention in the medical field, especially studying the electrical conductivity of whole blood samples and the like.

Specifically, with reference to FIGS. 1-3 and 8, the system, according to the subject invention, comprises an instrument, generally designated as 10, and a disposable blood sample card or carrier, generally designated as 12. The instrument 10 is a hand-held battery operated device used for the fast and simple measurement of blood conductivity, such as hematocrit and an approximation of hemoglobin. The instrument accepts the disposable sample card, which is used for the one-time conveyance and application of a liquid sample, such as blood, to the instrument.

The instrument 10 has provision for digital displays 14 for read-outs of hematocrit and the approximate equivalent of hemoglobin. There are no external switches on the instrument, and power is automatically applied when the disposable sample card 12 is inserted into the instrument.

In a preferred embodiment, the blood sample card, as best seen in FIGS. 4-7, is a micro-volume conductivity or measurement cell precision molded from plastic with built-in stainless steel alloy electrodes. Basically, the sample card 12 comprises a planar base portion 16 on which is defined a capillary tube 18. A nozzle 20 located at the end of the capillary tube, provides an entrance for a blood sample to enter the capillary tube. First and second electrodes 22 and 24 are disposed within the capillary tube in a spaced relationship and define a volume within the capillary tube. This volume, defined between the two electrodes within the capillary tube constitutes the conductivity or measurement cell 26.

Each of the electrodes 22 and 24 is electrically connected to a conductive disc or pad 28 and 30 that provides a means for associating the blood sample with the electronics 32 contained in the instrument to make a conductivity measurement of the liquid sample.

Again with reference to FIGS. 1-3, the instrument basically comprises an electronic portion 32 for processing data obtained from the blood sample on the sample card, a front end mechanism 34 for positioning the blood sample card within the instrument, and a digital display 14 for displaying in eye-readable form, the results of a heamtocrit measurement made in the instrument.

The front end mechansim 34 of the instrument 10 contains an indexing member 36 associated with a block or base portion 40 so that proper insertion of the sample card 12 within the instrument is assured. The base portion 40 is preferably made of a material exhibiting excellent heat conducting characteristics. One such material is aluminum.

A roller assembly, generally designated as 42, within the instrument holds or registers the sample card in intimate contact with the top surface of the base portion. Also provided as part of the front end mechanism is a generlly L-shaped bracket 44 which contains electrical contact assemblies 46 and 48. The L-shaped bracket is pivotally mounted in the mechanism so that, upon insertion of the sample card, the contact assemblies are brought into electrical association with the pads 28 and 30 on the disposable sample card 12.

Having briefly discussed the liquid conductivity measuring system, a detailed description of the disposable blood sample card and instrument will now be provided.

With reference to FIGS. 4-8, there is shown a preferred embodiment for the disposable blood sample carrier, generally designated as 12, which basically comprises a substantially planar body 16 that defines a capillary tube 18 within which are situated two spaced apart electrodes 22 and 24. The portion of the capillary tube 18 located between the electrodes 22 and 24 form a conductivity or measurement cell 26 wherein a blood sample resides during measurement of hematocrit. Associated with each of the electrodes are electrically conductive pads 22 and 24, respectively, which are used to interface the measurement cell 26 with the measuring instrument.

Figure 8:
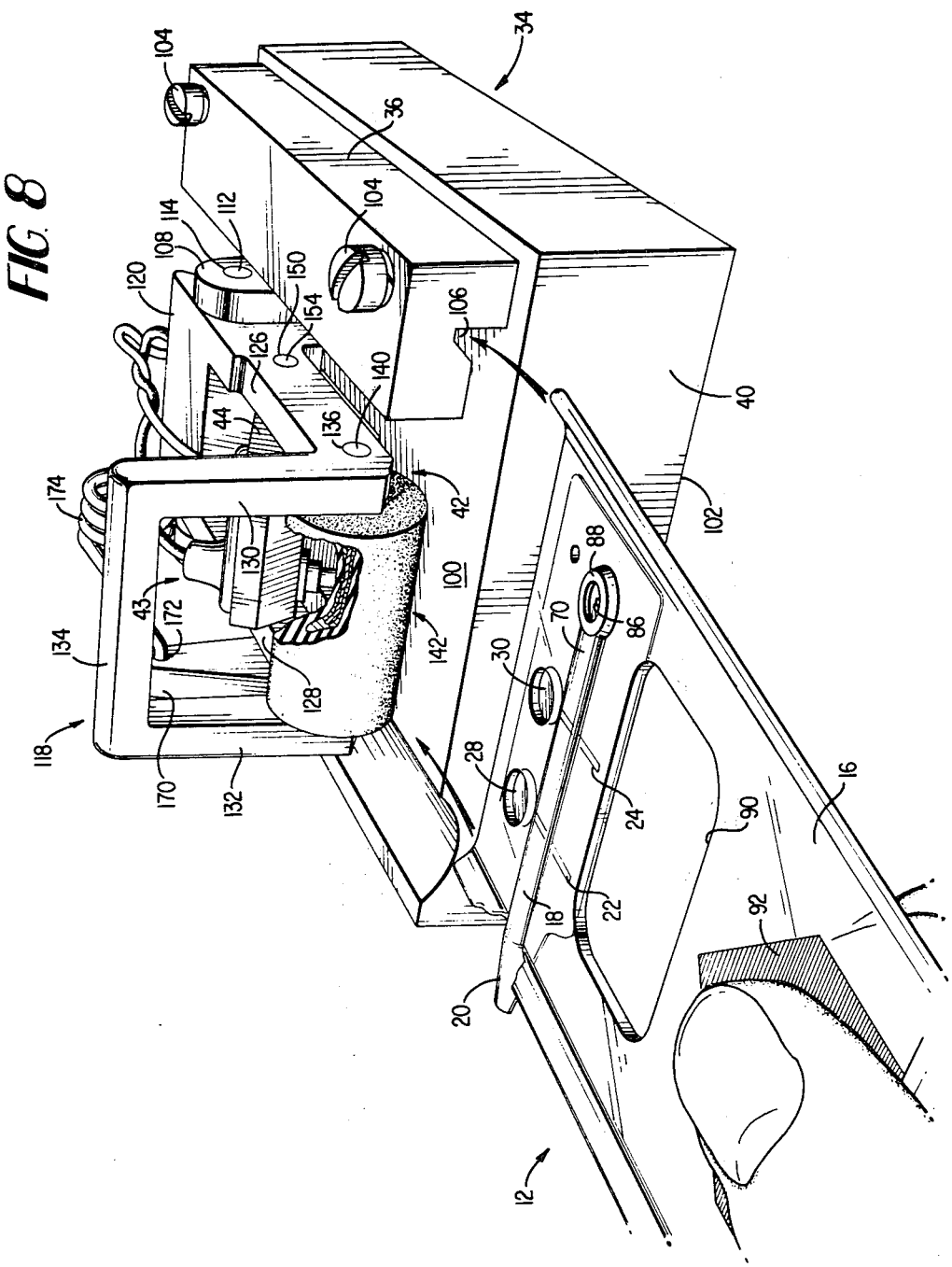
FIG. 8 is a perspective view showing an embodiment for the front end mechanism of the instrument with a sample card about to be inserted.
Figure 9:
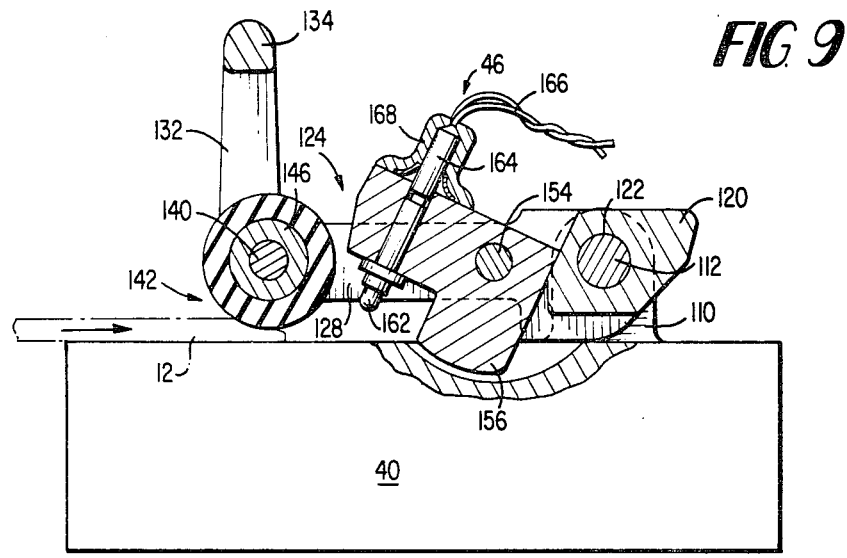
FIGS. 9 through 12 are longitudinal sections partially cut away from the front end mechanism shown in FIG. 8.

As best seen in FIGS. 4-7, the sample card 12 comprises an elongated substantially planar body portion 16 typically made from a translucent plastic material. The length of the body portion is typically 2.50 inches whereas the width of the body portion is typically 1.44 inches. With reference to FIG. 8, which shows the blood sample carrier in its position of intended use with respect to the measuring instrument along with FIGS. 4-7, the main body 16 defines a planar top surface 56 and a planar bottom surface 58. The body terminates in a front wall 60 and a rear wall 62. The sides of the body portion, each terminate in a wing portion 64 and 66 out of the plane defined by the top surface 56. When viewed in cross section, each of the wing portions is typically a curved section which deviates from planarity in a smooth and continuous fashion.

Near the front end of the main body portion there is defined a transversely extending raised portion 70, part of which interrupts wing portion 66 as it extends beyond the side wall of the main body. A semi-cylindrical transversely extending groove 72 is defined by the raised portion 70 on the bottom surface 58 of the body portion 12.

An overlay 74, typically made from a suitable plastic such as Mylar, is adhesively secured to the bottom surface 58 of the body portion. the overlay is die-cut so that it completely covers the semi-cylindrical groove and thus defines a capillary tube 18 having a nozzle portion 20 for receiving a blood sample either from the finger of a patient or from a test tube.

Adhesively secured to the overlay and interposed between the overlay and the bottom surface of the body portion are the pair of electrodes 22 and 24. The electrodes are positioned so that they extend transversely within the capillary tube and are spaced apart to define the measurement cell 26. Each of the electrodes terminate in a disc-shaped electrically conductive pad 28, 30 which is used in connection with the measuring instrument 10 in a manner to be described in greater detail hereinafter. The main body portion 16 contains a pair of apertures 80 and 82 which allow the measurement cell 26 to interface with the measuring instrument via the disc pads 28 and 30.

The other end of the capillary tube terminates in a fine aperture 86 which provides a means for evacuating the air within the capillary tube when the blood sample is being drawn into the tube by capillary action. A raised rim 88 completely surrounds the aperture and provides an interface for use with conventional, automatic liquid dispensers used in cleaning, testing and surfactant adding during manufacture of the sample card.

Near the capillary tube, the main body contains a large rectangular cut-out 90 which is used to decrease the thermal mass of the body portion in the area near the blood sample.

Additional structure and features of the blood sample carrier will be presented hereinafter when discussing the association between the sample card 12 and the instrument 10 used to make an automatic measurement of hematocrit.

With reference to FIGS. 8-17, the details of the mechanical front end mechanism 34 of the instrument 10 will now be described. The front end mechanism receives the sample card 12 in order to initiate measurement of hematocrit in the instrument. FIG. 8 shows the mechanism 34 in the position of intended use with the instrument housing 11 removed.

The front end mechanism 34 basically comprises a base portion 40 to which is attached an indexing block 36 for positioning the sample card when it is inserted into the instrument. Pivotally mounted to the reference block is a tension roller assembly 42 and an electrical contact assembly 43.

Basically, a disposable sample card 12 loaded with a blood sample is held with the molded indicating arrow 92 up and pointed toward the instrument and, then, inserted into the opening 94 provided on the facing edge of the instrument. The two contact assemblies 46 and 48 of the mechanism 34 make electrical contact with pads 28 and 30 of the sample card 12. The electronics portion 32 of the instrument probes the sample card, measures the conductivity of the blood sample, measures the front end block temperature, computes the hematocrit percentage and displays it on a digital display 14.

As shown in its position of intended use in FIG. 8, the front end mechanism 34 contains a base portion or reference block 40 which may take the form of a regular six-sided solid. The block defines a top surface 100 on which the sample card rides preparatory to positioning within the front end mechanism. The block also defines a bottom surface 102 by means of which the mechanism is mounted within the housing 11 of the instrument 10 by a suitable fastening means such as screws (not shown). The block is preferably made of a material which exhibits excellent heat conduction characteristics. One such material is aluminum.

Attached to the top surface of the block 40 is an elongated indexing member 36 which is fixed to the block by a suitable fastening means such as the screws 104. A groove 106 which mates with the wing portion 64 of the sample card extends along the length of the indexing member 36 a sufficient distance to permit the proper indexing of the sample card within the instrument.

Figure 13:
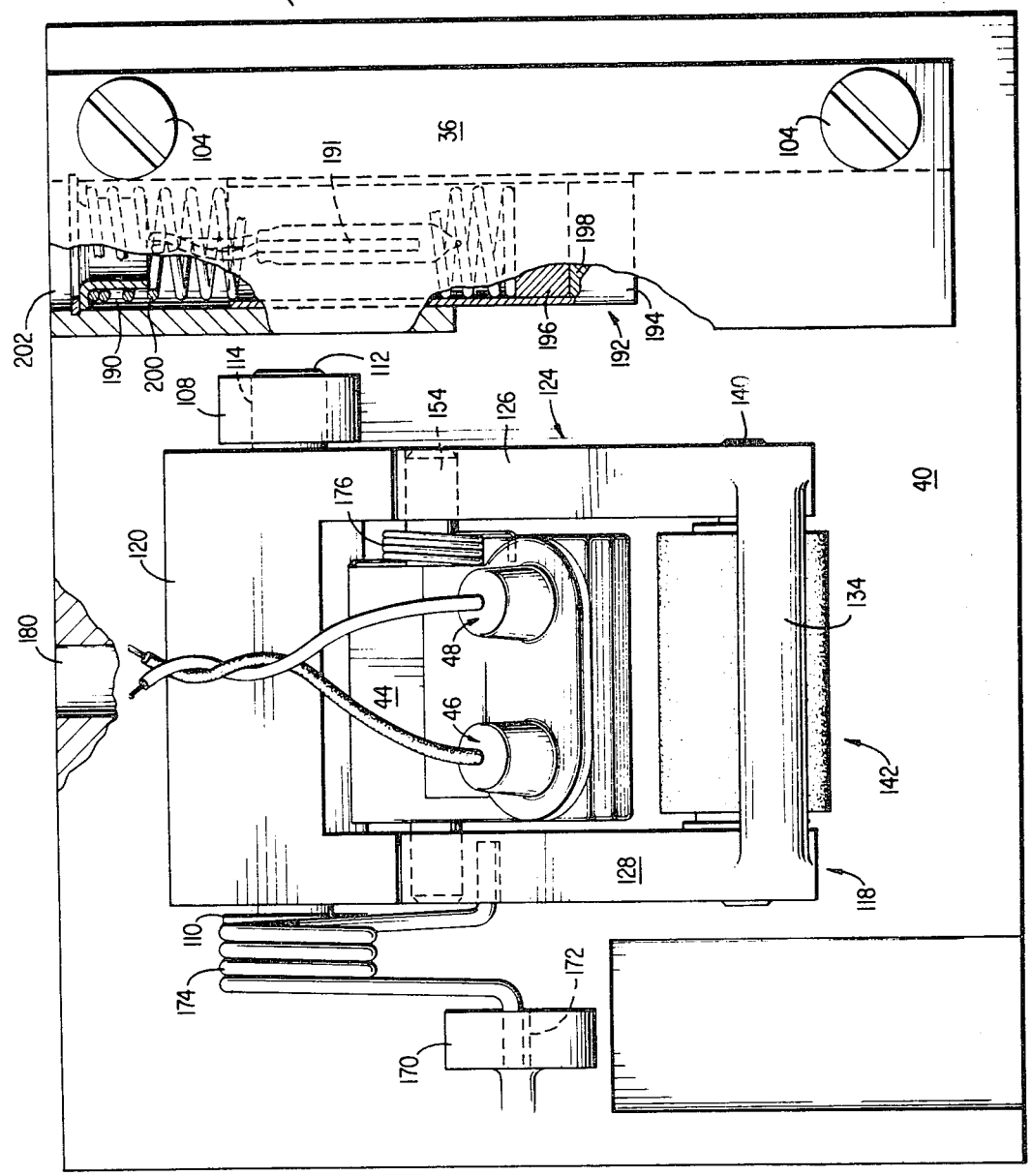
FIG. 13 is a top plan view of the front end mechanism shown in FIG. 8.
Figure 14:
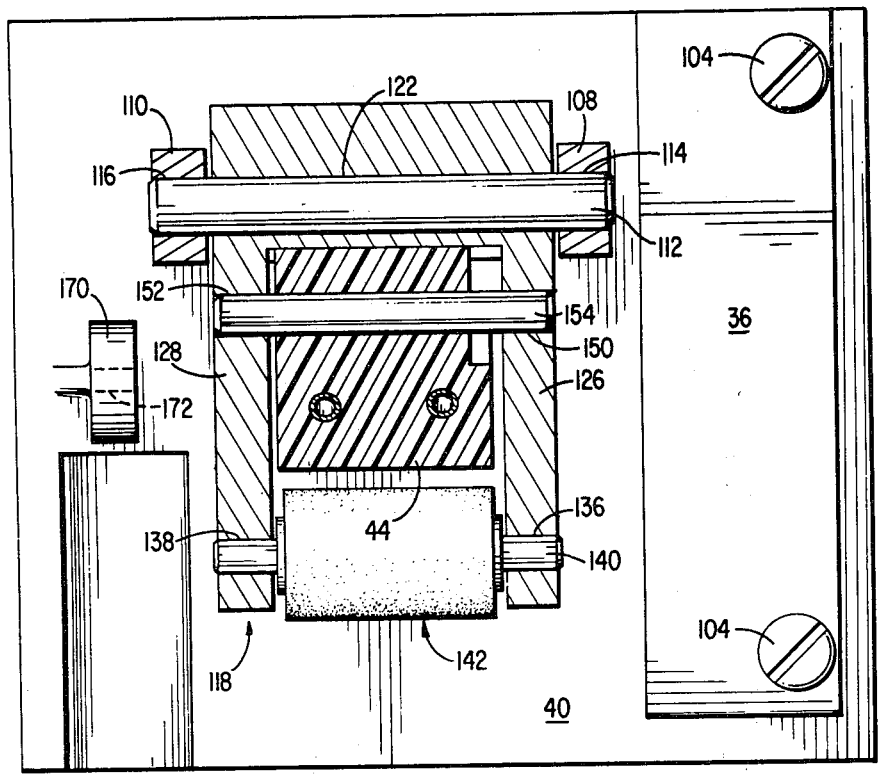
FIG. 14 is a top plan view of the front end mechanism shown in FIG. 8 and partially cut away to reveal the various pivot pins and their mountings.

As best seen in FIGS. 8, 13 and 14, positioned near the rear of the top surface in a spaced relationship are a pair of uprights 108 and 110. A pivot pin 112 is fixed within apertures 114 and 116 contained in the uprights 108 and 110, respectively, and provides a pivotal axis which is generally at a right angle to the guide groove 106 in the indexing member 36. A yoke 118 is pivotally mounted to the pivot pin 112. The yoke 118 comprises a body portion 120 with longitudinal bore 122 for receiving the pivot pin 112 and a transversely extending yoke structure generally designated as 124. The yoke structure 124 comprises a pair of transversely extending arms 126 and 128 which radiate from the body portion 120 in a direction toward the front of the instrument 10. Each of the arms terminates in a right angle upright 130 and 132. A cross bar 134 joins the uprights together.

In the yoke 118 where each upright 130, 132 meets an associated arm 126, 128, a bore 136, 138 is provided for receiving a pivot pin 140. As before, the pivot pin defines an axis which is substantially perpendicular to the groove 106 in the indexing member 36.

A resilient roller 142 comprising an outer tubing 144 and a hub 146 is rotatably mounted on the pivot pin 140. The tubing 144 is preferably made of a material which is resilient. One such material is amber latex. The hub 146, on the other hand, is typically made of nylon.

Each of the arms 126, 128 contains a bore 150, 152 which is positioned a short distance ahead of where the arm eminates from the body portion 120. A pivot pin 154 is fixed within the bores 150 and 152 so that the axis of rotation defined by the pivot pin is approximately perpendicular to the groove 106 in the indexing member 36. Pivotally mounted to the pivot pin is a generally L-shaped contact block 44 which is typically molded from Delrin. Positioned within the contact block are a pair of electrical contact assemblies 46 and 48 which are positioned in the block so that both of them will make contact with each of the disc pads 28 and 30, when the sample card is operatively inserted into the front end mechanism 34.

Figure 11:
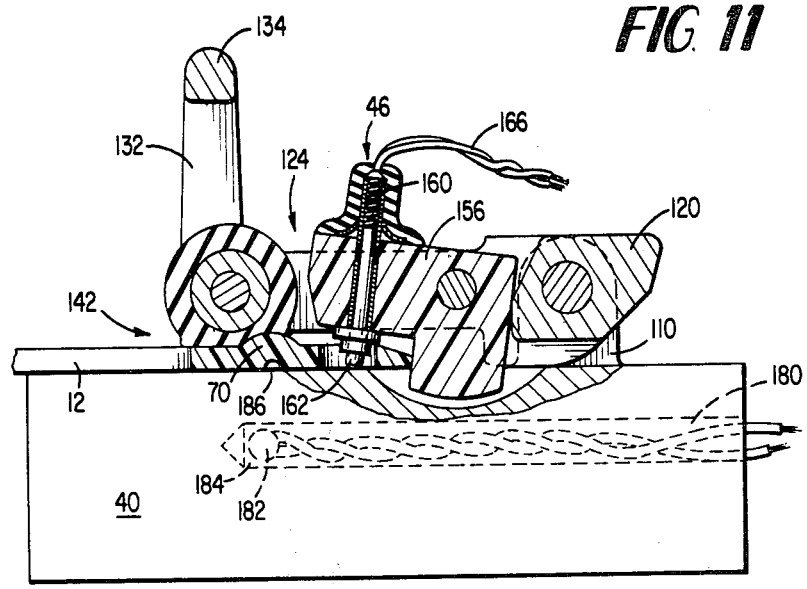

With reference to FIG. 11, each contact assembly is a conventional spring loaded contact mechanism. Using contact assembly 46 as exemplary, a compression spring 160 constantly urges the contact point 162 out of the assembly. In this way, a reliable contact is obtained between the contact point 162 and the steel pad 28 when the sample card is inserted into the instrument.

A connection point 164 for the contact assembly 46 is provided on the opposite side of the contact block 44 away from the contact point 162. An electrical wire 166 is attached to the connection point, and the contact assembly in this area is covered with a molded boot 168 which is typically made of sylastic.

Figure 16A:
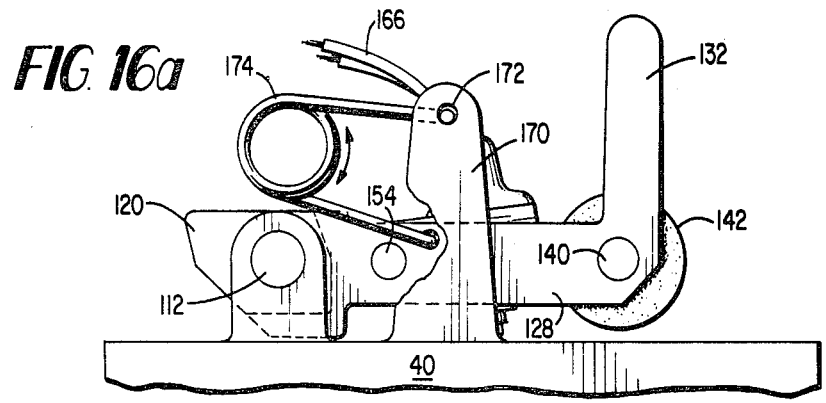
FIG. 16a, 16b and 17 are partial side views showing the yoke and roller assembly of the front end mechanism shown in FIG. 8.

With reference to FIGS. 13 and 16a, spaced from and slightly ahead of upright 110 is a stanchion 170 which contains an aperture 172 for receiving one end of a torsion spring 174. The other end of the torsion spring 174 is secured to the arm 128 of the yoke 118. This spring 174 acts to urge the yoke 118, and thus the resilient member 142, against the top surface 100 of the reference block 40. A second torsion spring 176 (FIG. 17) is positioned on the pivot 154 and has one leg pressing against the underside of the contact block 44 and the other leg pressing against the top surface 100 of reference block 40. This torsion spring 176 acts to constantly urge the contact assemblies 46 and 48 of the contact block 44 away from the top surface 100 of the reference block 40.

As best seen in FIGS. 13 and 11, a bore 180 is provided in the reference block for receiving a thermistor 182 which is potted in place within the bore. The termination area 184 of the bore 180 is chosen so that the thermistor is located relatively close to the portion of the top surface 100 where the blood sample will be located when the sample card is inserted. This general area is denoted as 186 in FIG. 11.

Figure 15:
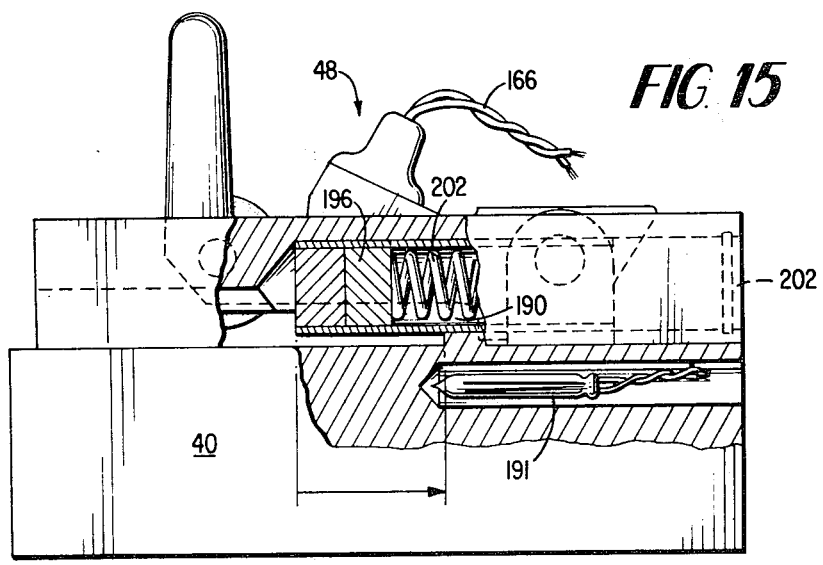
FIG. 15 is a side view partially cut away of the front end mechanism shown in FIG. 8.

With continued reference to FIGS. 13 and 15, the indexing member 36 contains an elongated cavity 190 which extends from the rear of the indexing member to well within the indexing groove 106. Positioned within the cavity is a member 192 that has a shape which closely resembles the cross-section of the cavity 190 so that the member 192 may be slidably mounted within the cavity. In a preferred embodiment, the member 192 has a cylindrical shape which mates with the generally cylindrical shape of the cavity.

The cylindrical member 192 typically comprises a tube or shell 194 within which is secured a permanent magnet 196. The permanent magnet is preferably a samarium cobalt magnet which is potted within the tube through the use of a suitable epoxy 198. The cylindrical member 192 is positioned within the cavity 190 so that it presents itself within the groove 106 of the indexing member 36. Positioned behind the magnet within the cavity is a compression spring 200 which constantly urges the magnet member 192 forward. The magnet member 192 and spring 200 are held within the cavity by a suitable cap 202 closing the rearward portion of the cavity.

Having discussed the structural details of the sample card 12 and the front end mechanism 34, a discussion of how they interrelate with each other to accomplish proper presentation of a blood sample to the instrument 10 for subsequent hematocrit measurement will now be discussed.

The disposable blood sample card 12 and the instrument 10 constitute the present system for measuring hematocrit. In essence, the blood sample carrier 12 is a micro-volume (typically 0.02 cc) conductivity cell. It is a precision molded plastic part with built-in stainless steel alloy electrodes 22 and 24. The blood sample card assures isolation of the blood sample from either the operator or the instrument. Among the advantages of the blood sample card are that it is used directly as supplied from the manufacturer, pre-conditioning is not required, and, after its one-time use, it is discarded leaving no post-measurement clean-up.

The blood sample contained in the capillary tube 18 of the sample card 12 is used directly as it comes from the patient with no pre-dilution or anti-coagulant additive steps. The disposable blood sample card is loaded with a blood sample in the following manner. In the case of a patient, the area, such as the finger or earlobe, where the blood sample is to be drawn, is first cleaned with isopropyl alcohol. The area is then allowed to dry after which it is punctured with a lancet. The first drop of blood is wiped away with a clean gauze. Without squeezing the sample area, the nozzle 20 of the sample card is placed against the puncture site, and the blood sample is drawn into the capillary tube 18 by capillary action. Blood should fill the capillary tube 18 such that it covers both electrodes 22 and 24 and the volume 26 between them. The blood sample must be free of air bubbles, foam, clots, etc. It may sometimes be necessary to tap the disposable sample card to enhance capillary action.

In the case of a laboratory sample, the blood sample is mixed gently with an anti-coagulant which is added when the original veni-puncture is taken. It is not necessary to add additional anti-coagulant. The nozzle 20 of the sample card 12 is placed near the laboratory blood sample, and, as before, the blood sample is drawn into the capillary tube 18 by capillary action.

In loading the sample card with the blood sample, certain advantageous aspects of the card are noted. The blood sample carrier is translucent so that the user can hold the blood sample carrier up to the light, look through it, and ensure that there are no discontinuities in the blood sample. The capillary section 70 provides a magnifying area so that any small air pockets or discontinuities in the blood sample are more readily apparent.

In order to make an accurate hematocrit measurement, it is necessary to know two things about the blood: blood conductivity and temperature. As is readily apparent, the volume 26 within the capillary tube 18 of the sample card, is so small that it would be very difficult to obtain the temperature of the blood sample directly. Therefore, an alternative approach is presented in the present invention.

When a reading is to be taken, the blood sample card is pressed into intimate contact with top surface 100 of the reference block 40 of the front end mechanism 34 which forms part of the instrument 10. The reference block 40 is made of a material which has excellent heat conducting characteristics. One such material is aluminum. Thus, with the blood sample card pressed against the block, the temperature of the blood is forced to the temperature of the block. The thermistor 182 imbeded in the block thus gives an accurate reading of the temperature of the blood.

In inserting the disposable sample card within the instrument to obtain a hematocrit reading, the blood sample card is oriented with respect to the entrance 94 of the instrument 10 so that the arrow 92 on the card points to the entrance of the instrument and the bump 70 in the capillary tube 18 is uppermost. The sample card is then inserted within the front end mechanism 34 of the instrument so that the wing 64 of the card rides in the groove 106 of the indexing member 36 (FIG. 8).

Figure 10:
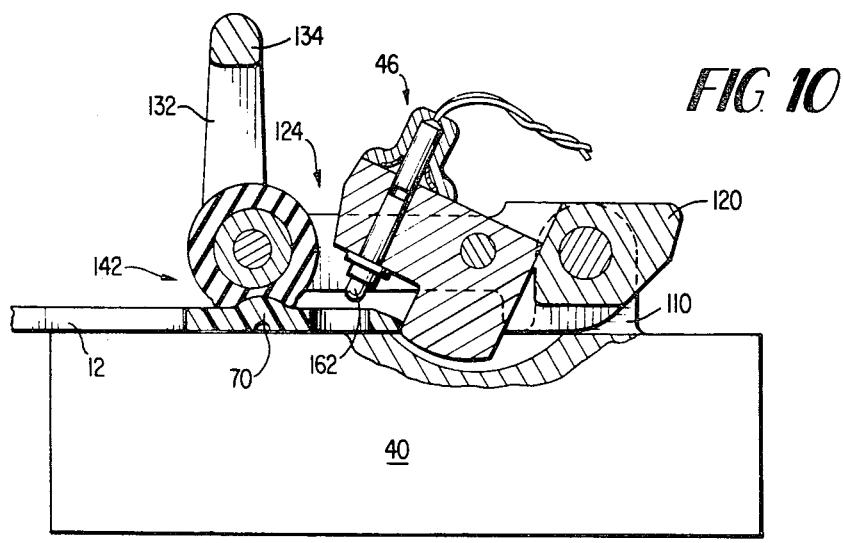

As the sample card rides in the groove 106 of the indexing member and along the top surface 100 of the block 40, the bump 70 in the capillary tube interfaces with the roller 142 (FIG. 10). As soon as the bump 70 passes under the roller 142, the torsion spring 174 urges the roller against the top surface 56 of the blood sample card and holds the bottom surface 74 of the card in intimate contact with the top surface 100 of the block 40 (FIG. 11).

The forward end 60 of the sample card 12 pushes against the L-shaped bracket 156 (FIG. 10), and the two contact assemblies 46 and 48 are forced down into the holes 80 and 82 in the sample card to make electrical contact with the pads 28 and 30 which are associated with the two electrodes 22 and 24 (FIG. 11). Because the contact assemblies are spring loaded, a reliable contact between the contact points 162 of the assemblies 46, 48 and the pads 28, 30 is ensured.

After a reading has been obtained, the sample card is removed and the L-shaped bracket 156 moves into its original position. The capillary tube bump 70 of the sample card 12 again bumps under the roller 142 and, after passing under the roller, the sample card may be freely removed.

Figure 12:
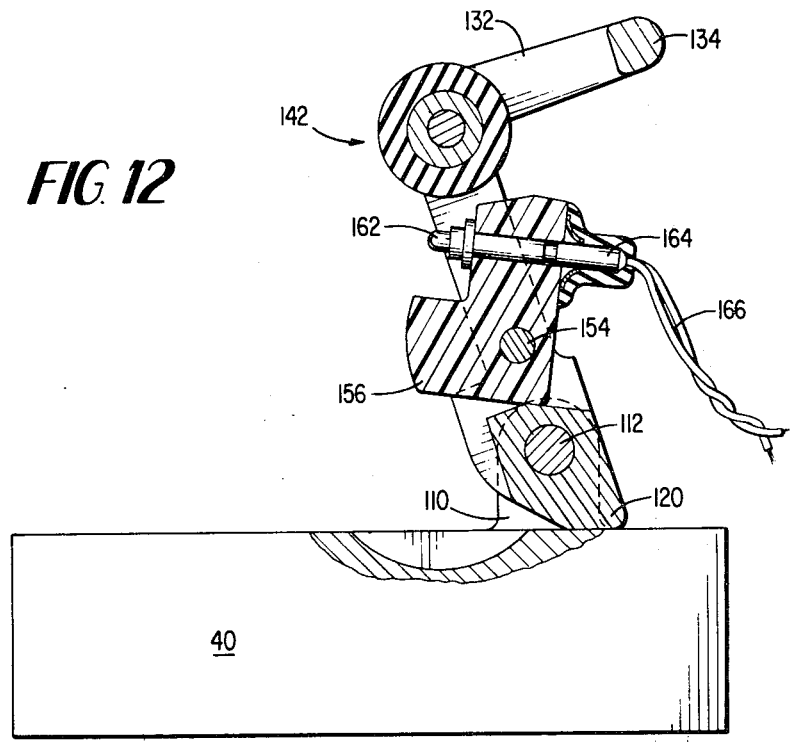
Figure 16B:
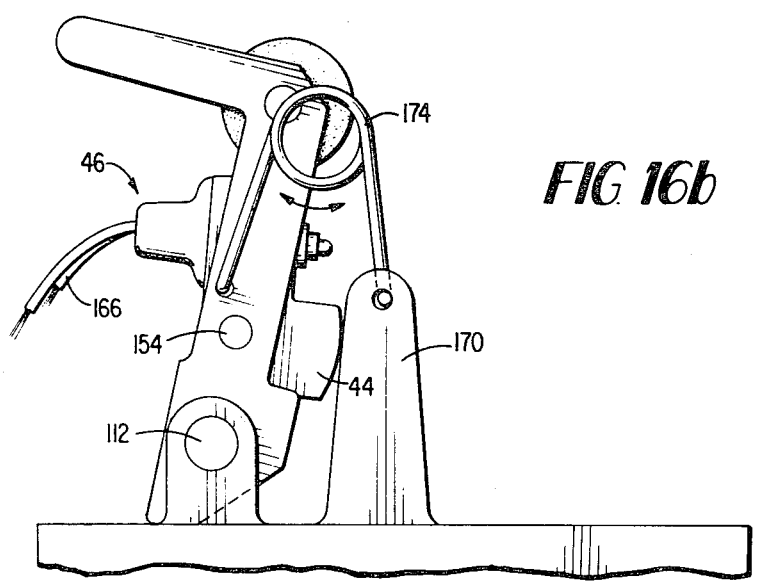
Figure 17:
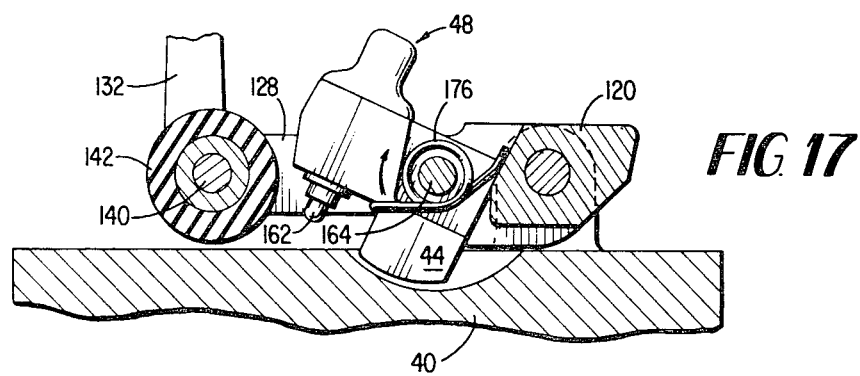

One avantageous feature of the instrument 10, is the ease with which the contact assemblies 46 and 48 may be cleaned. The instrument 10 contains a cover 220 (FIGS. 1 and 2) which may be flipped up to reveal the yoke 118 and roller assembly 42. An operator may grasp the cross piece 134 of the yoke and draw the assembly 42 out of the top cover, as shown in FIGS. 12 and 16b. This presents the contact assemblies 46, 48 and the surrounding areas in an easy to clean attitude so that the whole block area where blood might have congealed and formed can be cleaned.

Figure 18:
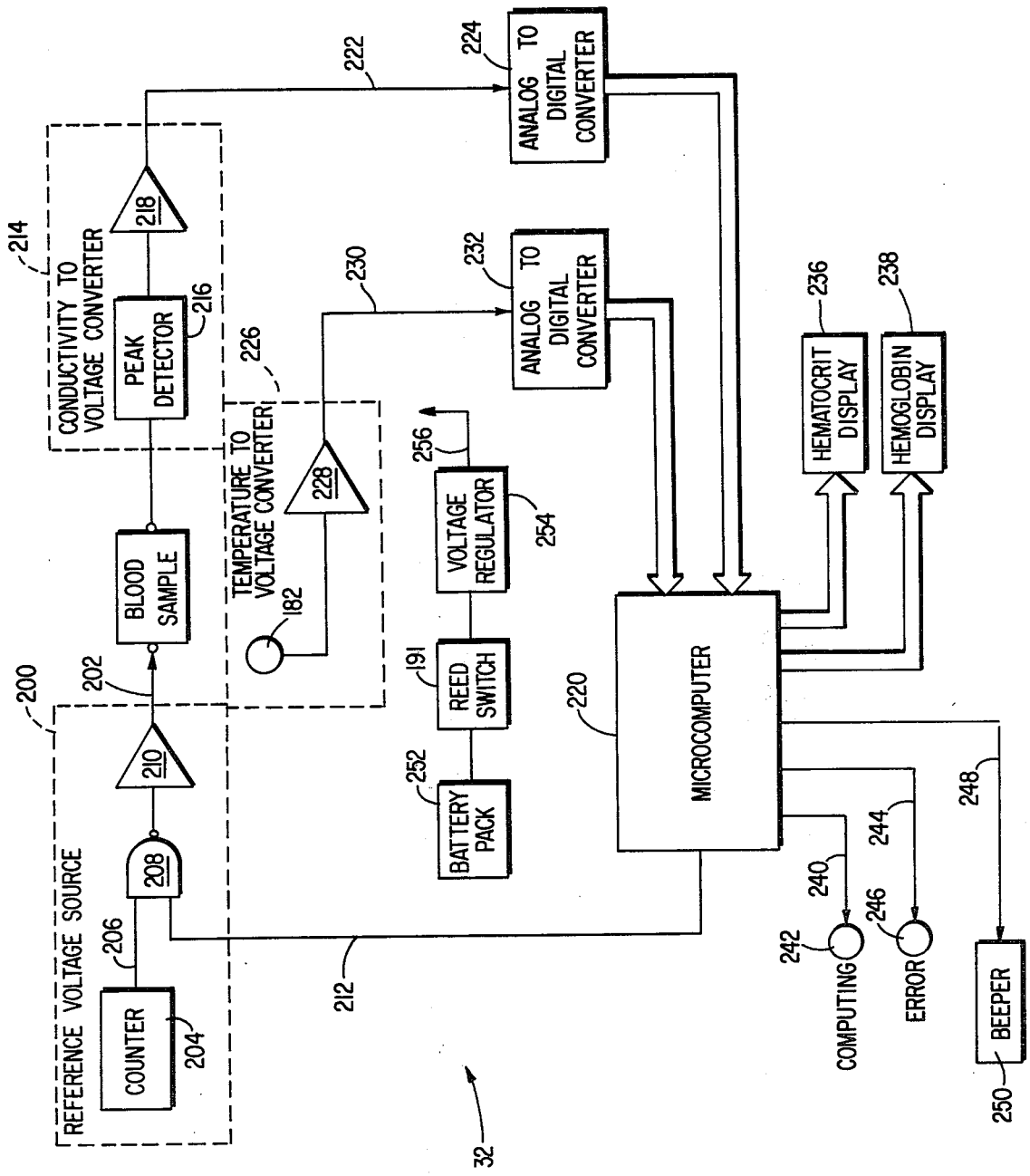
FIG. 18 is a block diagram showing the electronic circuitry associated with the instrument.

The electronic circuitry associated with producing a visual read-out of hematocrit and an approximation of hemoglobin in the blood sample under test is shown in diagrammatic form in FIG. 18. A reference voltage source 200 has its output 202 operatively connected to the electrodes 22, 24 of the sample card 12 via pads 28, 30, contact assemblies 46, 48 and leads 166. The reference voltage source is an AC-coupled square wave generator with zero DC component and has a square wave frequency of approximately 25 KHz. The output on line 202 is produced by a counter 204 which generates the 25 kHz square wave signal on line 206. This signal is fed into a nand-gate 208 the output of which appears on line 202 after passing through an amplifier 210. As will be explained hereinafter, a signal from a micro-computer 220 appears on line 212 and is fed into the nand-gate. In this way, the excitation current produced by the reference voltage source is impressed across the blood sample once every four seconds for a duration of approximately 0.5 seconds under the control of the microcomputer.

In addition, the electrodes 22, 24 of the sample card 12 are connected to the input of a conductivity-to-voltage converter 214 via pads 28, 30, contact assemblies 46, 48 and leads 166. The conductivity-to-voltage converter 214 comprises a peak detector 216 in series with an amplifier 218. The output of amplifier 218 is fed via line 222 into an analog-to-digital converter 224.

The temperature of the blood sample under test is converted to analog voltage by a temperature-to-voltage converter 226, which comprises thermistor 182 in series with an amplifier 228. The output of amplifier 228 is fed via line 230 to an analog-to-digital converter 232.

The microcomputer 220 is of conventional design and, in a preferred embodiment, is of the type carrying the designation 8748/8048 and is manufactured by Intel Corporation of Santa Clara, California. The microcomputer takes the digital outputs of the analog-to-digital converters 224 and 232 and processes the data in a manner to be described in detail hereinafter to produce a display of hematocrit on hematocrit display 236 and an approximation of hemoglobin on display 238. The displays 236 and 238 are of conventional design and, in a preferred embodiment, each takes the form of a three digit LED display.

The microcomputer 220 also produces a signal on line 240 which activates a light 242, such as an LED, to indicate that the instrument is computing. The microcomputer also produces a signal on line 244 to activate a light 246 to indicate an error. Finally, the microcomputer produces a signal on line 258 to intermittently activate a conventional beeper 250. The details of the computing, error and beeper signals will be described in detail hereinafter. The circuitry associated with the instrument is powered by a battery pack 252. When the reed switch 191 is closed, the voltage from the battery pack passes through a voltage regulator 254, the output of which appears on lines 256. The output of the voltage regulator is used to power the electronic circuitry of the instrument.

Having described the components constituting the electronic circuitry of the instrument, an explanation of the operation of this circuitry will now be provided. As is well known, as current is passed through the blood, the blood tends to polarize at the electrode faces and conductivity is reduced with time. This effect is minimized through the use of the particular reference voltage source. In this way, conductivity through the blood varies in a square wave manner. The peak detector 216 in circuit with the amplifier 218 is connected across the electrodes 22 and 24 of the blood sample carrier 12 in the same manner as the reference voltage source 200. The peak detector 216 ensures that the conductivity amplitude of the blood sample is measured just after the square wave leading and trailing edges. This minimizes inaccuracy that would otherwise be obtained due to polarization of the blood. The peak detector signal is amplified and then presented to the A-to-D converter 224.

The signal generated by the thermistor 182 after being amplified by amplifier 228 is presented to another A-to-D converter 232. It is to be understood that the A-to-D converters 224 and 232 may be replaced by a single A-to-D converter used in conjunction with a conventional multiplexer that receives and multiplexes the peak detector and therminstor signals.

Thus, A-to-D converter 224 has as its output a digital signal representative of conductivity of the blood sample in the disposable sample card, while the second A-to-D converter 232 has as its output a digital signal representative of the temperature of the blood sample. These outputs are fed into the microcomputer 220 which, through the use of look-up tables, provides a signal to the hematocrit display 236 for presentation of the hematocrit reading in an eye-readable format and to the hemoglobin display 238 for presentation of an approximation of the hemoglobin in an eye-readable format.

Before consulting the look-up tables, the microcomputer insures that two conditions are present. The first condition is that two consecutive conductivity signals obtained from the output of A-to-D converter 224 are within approximately 0.1 hematocrit percentage of each other. the second condition is that two consecutive temperature signals from the output of A-to-D converter 228 are within approximately 0.1° C. of each other. When both conditions are met, the microcomputer interrogates the look-up tables and produces a signal indicative of temperature-compensated hematocrit percentage.

In a preferred embodiment of the conductivity measuring system, the look-up tables, which are permanently stored in memory, were generated by carrying out conductivity test over a known temperature range for blood samples having known hematocrit percentage. A family of curves were generated and digitized for storage within the microcomputer memory in the following manner. For a given temperature within the range of 10°–46° C., the conductivity of a sufficient number of blood samples having known hematocrit percentage in the range of 7–80 percent were tested. This was repeated a sufficient number of times for various temperatures within the previously stated range. At this same time, a test was made of the conductivity of a blood sample having a known hematocrit percentage over the recited temperature range to show the effect that temperature had on the conductivity of the sample. This procedure was repeated for various blood samples having known hematocrit percentage in the range of 7–80 percent. In this way, a set of temperature compensation curves were generated. This information was then permanently stored within the microcomputer memory.

Thus, when the microcomputer wishes to produce the signal indicating temperature-compensated hematocrit percentage, the microcomputer takes the conductivity signal from the A-to-D converter 224 and in response thereto selects the appropriate look-up table which yields a hematocrit percentage based on the detected conductivity of the blood sample under test. At the same time, the microcomputer takes the temperature information from the output of the A-to-D converter 232 and interrogates the appropriate look-up table to determine the amount of compensation necessary based on the temperature of the sample being tested. Then, the correction factor is either added to or substracted from the uncompensated conductivity reading to produce the signal indicative of temperature-compensated hematocrit percentage. This signal is then displayed in an eye-readable form as hematocrit percentage.

To ensure that the instrument is functioning properly, the micro-computer 220 employs conventional control techniques to provide the operator with a visual indication of instrument operation. Light 242 flashes for the duration of whatever time it takes for the blood sample to stabilize, thus, indicating that the instrument is computing. The stabilization time is typically between 10 and 40 seconds. After, the microcomputer has looked up the hematocrit percentage in the look-up tables contained in the computer memory, the light 242 is extinguished and the hematocrit percentage is displayed as a visual read-out on hematocrit display 236.

The memory of the microcomputer contains look-up tables for a hematocrit range between 10 and 70 percent. Therefore, if the computer is unable to find a listing based on the conductivity and temperature information provided to it, the computer then causes error light 246 to blink. If, at the end of a predetermined period of time, for example 40 seconds, a valid reading is not obtained, the error light 246 continues to blink.

Under control of the microcomputer, the beeper 250 beeps the instant the disposable sample card is properly positioned within the instrument. The beeper is quiet throughout the testing of the blood sample, and then beeps again when the hematocrit and hemoglobin readings are displayed. Thereafter, the beeper beeps every ten seconds to alert the operator that the disposable is still contained within the instrument and that the instrument is operative, which could lead to drainage of the battery. The microcomputer also causes the beeper to be activated whenever the error light 246 is on.

The battery pack 252 is positioned within the instrument as shown in FIG. 2. The battery pack in a preferred embodiment employs seven rechargeable nickel-cadmium cells. It is contemplated that the cells may be charged while they are inside the unit or when they are outside the unit since a charging jack 256 is part of the battery pack. With reference to FIG. 2, the charging jack is accessible through a slot 258 in the side of the instrument 10 when the battery pack is placed in the instrument and is directly accessible when the battery pack is outside the instrument.

The instrument also has a carrying handle 260 and a storage compartment 262 for storing the pre-packaged disposable sample cards.

Although the present invention has been shown and described in terms of a preferred embodiment, it will be appreciated by those skilled in the art, that changes or modifications are possible which do not depart from the inventive concepts described and taught herein. Such changes and modifications are deemed to fall within the purview of these inventive concepts.

What is claimed is:

1. A system for measuring temperature-dependent parameters of a liquid sample, said system comprising:
    a base portion made of a material exhibiting excellent heat transfer characteristics;
    detecting means for detecting the temperature of said base portion;
    a disposable sample card for confining a predetermined volume of said liquid sample in intimate contact with said base portion wherein, after a period of time, said liquid sample assumes the temperature of said base portion;
    electrode means immersed within said predetermined volume of said liquid sample; and
    means connected to said electrode means and said detecting means for producing a signal indicative of the temperature-dependent parameter being measured.

2. The system of claim 1, further comprising means for displaying said signal indicative of the temperature-dependent parameter in eye-readable format.

3. The system of claim 1, wherein said material for said base portion is aluminum.

4. Apparatus for measuring parameters of a liquid sample contained in a liquid sample carrier having a guide member and a registration member, said apparatus comprising:
    a base portion;
    indexing means cooperating with the guide member for ensuring proper insertion of said carrier into said apparatus; and
    carrier-holding means cooperating with the registration member for ensuring proper registration of said carrier into said apparatus.

5. The apparatus of claim 4, wherein said indexing means comprises a guide channel configured to mate with the guide member of said carrier.

6. The apparatus of claim 4, wherein said carrier-holding means comprises yieldable biasing means for holding said carrier in intimate contact with said base portion.

7. A system for measuring parameters of a liquid sample, said system comprising a liquid sample carrier and a measuring apparatus,
    (A) said carrier including;
        (a) a body portion,
        (b) sample-receiving means on said body portion for receiving a liquid sample,
        (c) electrode means disposed within said sample-receiving means,
        (d) guide means for ensuring proper insertion of said carrier into said apparatus, and
        (e) registering means for ensuring proper registration of said carrier in said apparatus, and
    (B) said apparatus including;
        (a) a base portion,
        (b) indexing means cooperating with said guide means for ensuring proper insertion of said carrier into said apparatus,
        (c) carrier-holding means cooperating with said registering means for ensuring proper registration of said carrier in said apparatus.

8. The system of claim 7, wherein said apparatus further includes:
    electronic circuitry means for measuring a parameter of said liquid sample, and
    means for electrically connecting said electronic circuitry means with said electrode means when said carrier is properly inserted and registered in said apparatus.

9. The system of claim 7, wherein said apparatus further includes means responsive to the proper insertion and registration of said carrier in said apparatus for activating said electronic circuitry.

* * * * *